(12) United States Patent
Li et al.

(10) Patent No.: US 11,925,435 B2
(45) Date of Patent: Mar. 12, 2024

(54) INTRA-ORAL SCANNING DEVICE WITH INTEGRATED OPTICAL COHERENCE TOMOGRAPHY (OCT)

(71) Applicant: D4D Technologies, LLC, Richardson, TX (US)

(72) Inventors: Ye Li, Plano, TX (US); Justin G. Graham, Wylie, TX (US); Rod A. Duncan, Lucas, TX (US); Greg R. Basile, Dallas, TX (US); Grant E. Kenworthy, Allen, TX (US); Henley S. Quadling, Dallas, TX (US); Mark S. Quadling, Plano, TX (US); Glen Freeman, Plano, TX (US)

(73) Assignee: D4D Technologies, LLC, Richardson, TX (US)

( * ) Notice: Subject to any disclaimer, the term of this patent is extended or adjusted under 35 U.S.C. 154(b) by 0 days.

(21) Appl. No.: 17/836,606

(22) Filed: Jun. 9, 2022

(65) Prior Publication Data
US 2022/0296103 A1 Sep. 22, 2022

Related U.S. Application Data

(63) Continuation of application No. 16/298,613, filed on Mar. 11, 2019, now Pat. No. 11,382,517.

(51) Int. Cl.
*A61B 5/00* (2006.01)
*A61C 9/00* (2006.01)
(Continued)

(52) U.S. Cl.
CPC .......... *A61B 5/0088* (2013.01); *A61B 5/0066* (2013.01); *A61C 9/0053* (2013.01);
(Continued)

(58) Field of Classification Search
CPC ... A61B 5/0088; A61B 5/0066; A61B 5/1077; A61B 5/4547; A61C 9/0053;
(Continued)

(56) References Cited

U.S. PATENT DOCUMENTS 9,820,655 B2 * 11/2017 Ramanujam ......... A61B 5/0084
2007/0146726 A1 6/2007 Quadling et al.
(Continued)

FOREIGN PATENT DOCUMENTS

WO 2007084727 7/2007

OTHER PUBLICATIONS

International Search Report and Written Opinion, PCT/US2020/021944, dated Jul. 13, 2020.
(Continued)

*Primary Examiner* — Nasim N Nirjhar
(74) *Attorney, Agent, or Firm* — Scheef & Stone, LLP

(57) ABSTRACT

An intra-oral scanning device includes a light source and an optical system, and communicates with a display system. The device provides for more efficient transmission and capture of images. It integrates OCT scanning with RGB-based scanning. In operation, the device is used for recording topological characteristics of teeth, dental impressions, or stone models by digital methods and for use in CAD/CAM of dental restorative prosthetic devices. To that end, the RGB-based scan obtains surface data (e.g., a margin), while the OCT scan penetrates the surface. The two scanners operate from within the same physical housing and preferably at the same time such that only one scanning pass (to obtain all necessary data) is required. The 3D data obtained from the OCT scan is registered with the 3D data obtained from the RGB-based scan by virtue of being captured using a common return path. Preferably, the 3D surface data is used to align the volume data, such that the OCT scan
(Continued)

operates over a much sparser scanning volume than would otherwise be required if the OCT scan were carried out separately. In this manner, there is less stitching of data required to build the output images, thereby enabling a "one-pass" operation.

16 Claims, 8 Drawing Sheets

(51) Int. Cl.
*G01B 9/02004* (2022.01)
*G01B 9/02091* (2022.01)
*G01B 11/24* (2006.01)

(52) U.S. Cl.
CPC ...... *G01B 9/02004* (2013.01); *G01B 9/02091* (2013.01); *G01B 11/2441* (2013.01)

(58) Field of Classification Search
CPC ............... A61C 9/006; G01B 9/02004; G01B 9/02091; G01B 11/2441; G01B 11/2518
See application file for complete search history.

(56) References Cited

U.S. PATENT DOCUMENTS

| | | | |
|---|---|---|---|
| 2008/0062429 A1 | 3/2008 | Liang et al. | |
| 2013/0236850 A1* | 9/2013 | Wu | A61C 9/006 433/29 |
| 2014/0146142 A1 | 5/2014 | Duret et al. | |
| 2014/0176958 A1 | 6/2014 | Flanders et al. | |
| 2016/0044253 A1 | 2/2016 | Dainty et al. | |
| 2016/0330355 A1* | 11/2016 | Tchouprakov | A61C 9/006 |
| 2017/0238897 A1 | 8/2017 | Siewerdsen et al. | |
| 2018/0027159 A1 | 1/2018 | Dillon et al. | |
| 2018/0028063 A1* | 2/2018 | Elbaz | H04N 13/271 |
| 2019/0231492 A1 | 8/2019 | Sabina et al. | |
| 2019/0302465 A1 | 10/2019 | Yu et al. | |
| 2019/0377134 A1 | 12/2019 | Yi et al. | |
| 2020/0129068 A1* | 4/2020 | Fan | A61B 5/0066 |
| 2021/0298582 A1* | 9/2021 | Moon | A61B 1/0005 |

OTHER PUBLICATIONS

Changsu, Jun et al., All-fiber wavelength swept ring laser based on Fabry-Perot filter for optical frequency domain imaging, Optical Society of America, Oct. 20, 2014, vol. 22, No. 21.
Katkar, Rujuta A. et al., Optical Coherence Tomography, Department of Comprehensive Dentistry, 2018, downloaded on Sep. 30, 2019 at Medical University of South Carolina.
Iftimia, Nicusor et al., Handheld optical coherence tomography-reflectance confocal microscopy probe for detection of basal cell carcinoma and delineation of margins, Journal of Biomedical Optics, Jul. 2017, 22(7), 076006.
Lenton, Patricia et al., Clinical cross-polarization optical coherence tomography assessment of subsurface enamel below dental resin composite restorations, Journal of Medical Imaging, Apr.-Jun. 2014, 1(1), 016001.
Zhao, Yang et al., Dual-axis optical coherence tomography for deep tissue imaging, Optics Letters, vol. 42, No. 12, Jun. 15, 2017.
Fercher A.F. et al., Optical coherence tomography-principles and applications, Institute of Physics Publishing, Rep. Prog. Phys. 66 (2003) 239-303.
Fried, Daniel et al., Optical Coherence Tomography in Dentistry, Tokyo Medical and Dental University, Jun. 20-21, 2013.
Fan, Chuanmao, True Depth Resolved Polarization Sensitive Optical Coherence Tomography, University of Missouri, Dec. 2012.
Tomlins, P. H., et al., Theory, developments and applications of optical coherence tomography, Institute of Physics Publishing, J. Phys. D: Appl. Phys. 38 (2005) 2519-2535.
Zavareh, Amir, Systems and Methods for the Spectral Calibration of Swept Source Optical Coherence Tomography Systems; Texas A&M University, Dec. 2019.

* cited by examiner

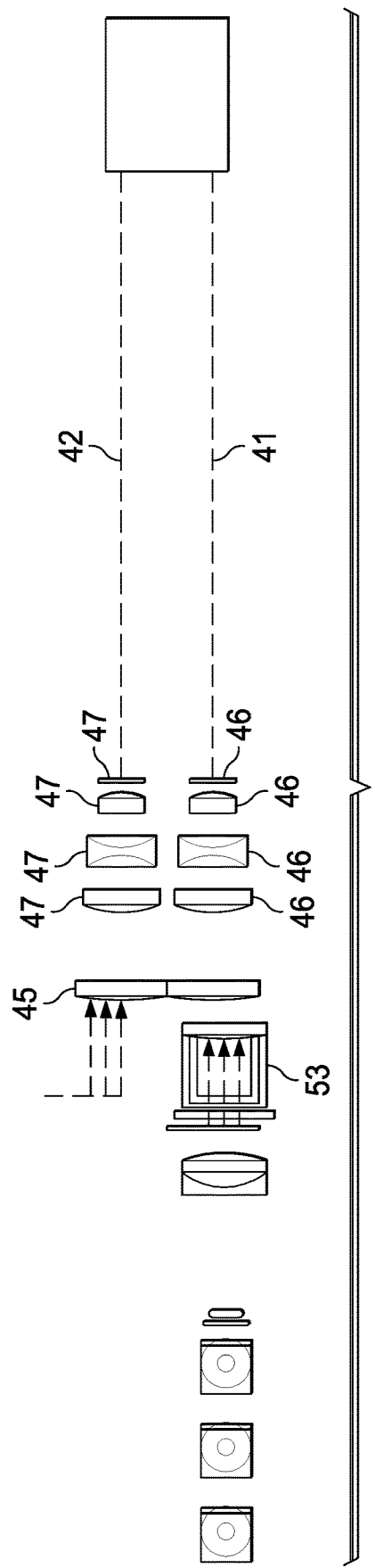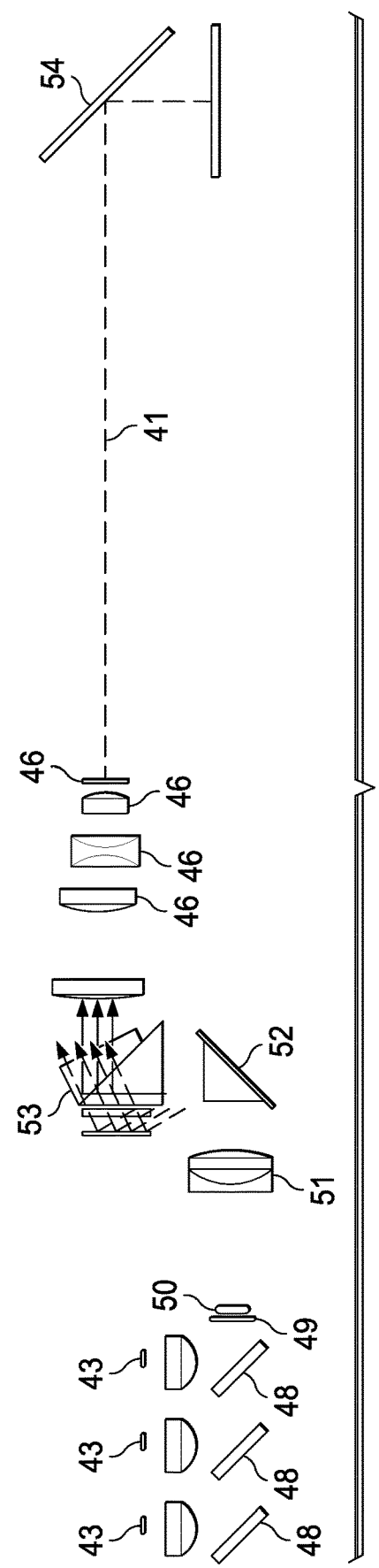

INTRA-ORAL SCANNING DEVICE WITH INTEGRATED OPTICAL COHERENCE TOMOGRAPHY (OCT)

CROSS-REFERENCE TO RELATED APPLICATION

This application is a continuation of U.S. patent application Ser. No. 16/298,613 filed on Mar. 11, 2019.

BACKGROUND

1. Technical Field

This disclosure relates generally to scanning devices.

2. Brief Description of the Related Art

It is known to provide an intra-oral scanner to enable a user to scan dental patients intra-orally. Such devices are used in a standalone scanner, or as part of a computer-aided design and manufacture (CAD/CAM) system. A CAD/CAM system typically uses dental CAD software executing on a laptop or desktop machine, optionally together with specialized milling machine hardware driven by machine control CAM software. The dentist first prepares a patient's damaged tooth anatomy (using standardized dental practices) to receive a dental restoration including, but not limited to, an inlay, an onlay, a veneer, a crown or a bridge. Once the preparation has been made, the dentist uses the scanner described and illustrated herein to capture a digital impression of a patient's dental anatomy. Once the digital impression has been captured the dentist is presented with an "initial proposal" restoration by the automated CAD software. This initial proposal preferably automatically selects an appropriate tooth anatomy, and it sizes it to fit onto the preparation and within the patient's existing "good" anatomy. This initial proposal is then customized by the dental professional, typically using specialized software tools to adjust and modify the design, with the goal of ultimately achieving an optimized design that fits into the patient's anatomy. Once the final 3D model of the tooth has been achieved, it is sent electronically to a milling machine (or third party), which then generates the actual restoration from the design.

Optical coherence tomography (OCT) is a known imaging technique that is based on an interferometer with a low coherence or wavelength swept laser source. When a swept laser source is used, for example, the laser sweeps through a wavelength or frequency range (e.g., 100 nanometers (nm) at center wavelength of 910 nm). The swept laser beam is split into two beam arms, namely, a reference arm, and a sample or signal arm. In operation, a backscattering beam from the sample arm, and the reflection beam from the reference arm, are combined and interfered at a photodiode detector only when an optical path difference from both arms are matched (i.e., when particular optical interference conditions are met). For a dental scan, and through the wavelength range of the swept laser source, the imaging in depth, also called an A-scan, is obtained from a test sample (such as enamel, dentin or tissue) due to the partial penetration of the laser beam into the sample. When a high speed swept laser source (e.g., at a rate of 1.5 MHz is used) and then combined with a two-dimensional (2D) MEMS scanning mirror, three-dimensional (3D) OCT volume data is generated at video speeds.

While existing scanner devices provide satisfactory results, there remains a need for improvements in scanning speed and accuracy as well as to provide enhanced margin detection of 3D geometry through blood, saliva and thin gingiva tissue.

BRIEF SUMMARY

In one embodiment, an OCT scanner is integrated within a same housing as a conventional intra-oral scan device that produces 3D optical scan data. The housing is configured to be held within a user's hand. In one embodiment, and to facilitate the OCT scanning, a high speed swept laser beam at a center wavelength (e.g., 910+/−50 nm) is delivered through a single mode fiber to an intra-oral scanner positioned within the housing. The laser beam is collimated with a fiber collimator and aligned to a two-dimensional (2D) MEMS scanning mirror, which scans the laser beam in X and Y directions. The scanned laser beam is coupled in a telecentric beam using an aspherical lens. The telecentric laser beam is then reflected from a beam splitter at a given angle (e.g., 45°), which reflects wavelengths at the center wavelength but transmits RGB wavelengths used in the 3D optical scan. The reflected beam for the beam splitter is projected through a lens projecting system, which preferably includes lenses with dual band anti-reflection coating for both the center wavelength and RGB wavelengths to pass through. A tip mirror in the device also reflects the center and RGB wavelengths. In operation, a backscattering beam from a test sample travels through a same path to the fiber and is combined with a reference at a photodetector to generate an OCT image.

Independently, and without interfering with the OCT laser and signal, the scanner projects RGB laser patterns and captures 3D images using a CCD sensor or the like. The OCT and RGB-based scanner are configured to operate both independently, but preferably they are configured and controlled to work in a combined manner to provide enhanced 3D imaging and dental diagnosis.

The intra-oral scanning device (which includes both OCT and the 3D RGB-based scanners as described) typically comprises a component of an optical impression system for computer-aided design (CAD) and manufacture (CAM) of dental restorations. In operation, the device is used for recording topological characteristics of teeth, dental impressions, or stone models by digital methods and for use in CAD/CAM of dental restorative prosthetic devices. To that end, the RGB-based scan obtains surface data (e.g., a margin), while the OCT scan penetrates the surface. As described above, the two scanners operate from within the same physical housing and preferably at the same time such that only one scanning pass (to obtain all necessary data) is required. When the two scanners are used together, the 3D data obtained from the OCT scan is registered with the 3D data obtained from the RGB-based scan. In particular, preferably the 3D surface data is used to align the volume data, such that the OCT scan operates over a much sparser scanning volume than would otherwise be required if the OCT scan were carried out separately.

The foregoing has outlined some of the more pertinent features of the subject matter. These features should be construed to be merely illustrative.

BRIEF DESCRIPTION OF THE DRAWINGS

For a more complete understanding of the disclosed subject matter and the advantages thereof, reference is now made to the following descriptions taken in conjunction with the accompanying drawings, in which:

FIG. 6A is a plan view of the optical system of the scanner;

FIG. 6B is an elevation view of the optical system;

DETAILED DESCRIPTION

As noted above, the scanner of this disclosure is a handheld optical scanner that is designed to be placed in a patient's mouth to create an image (typically a 3D image) of the teeth after preparation for dental restoration. The following describes an embodiment of the RGB-based components of the scanner (i.e. with the OCT components initially omitted).

Figure 1:
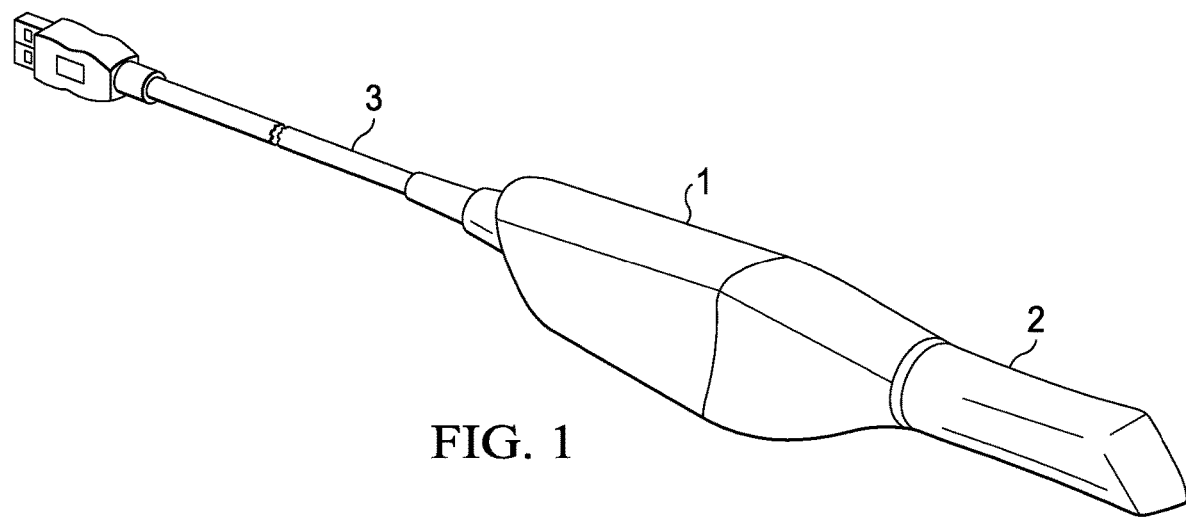
FIG. 1 depicts a perspective view of an embodiment of a hand-held scanner according to this disclosure.

In particular, FIG. 1 depicts a perspective view of the hand-held scanner in one embodiment. In this embodiment, the scanner preferably comprises a scanner body 1, a detachable scanner tip 2, and detachable data cable 3.

Figure 2:
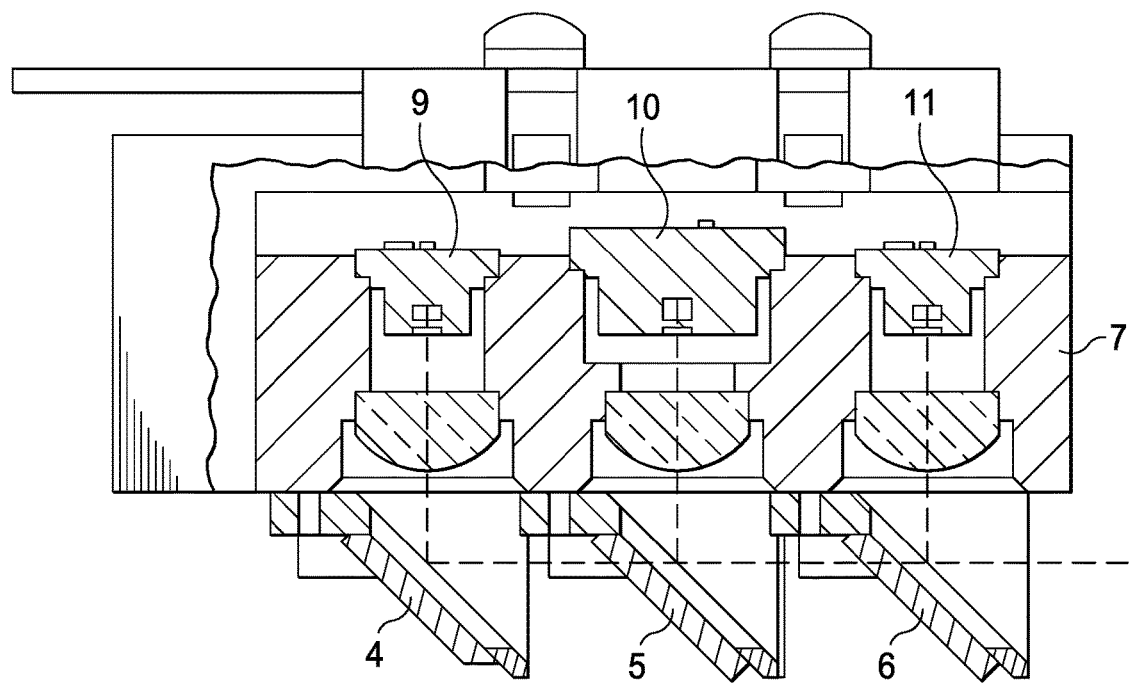
FIG. 2 depicts a light engine module of the scanner.

With reference now to FIG. 2, a light engine module of the scanner of FIG. 1 is shown in perspective. The light engine module preferably comprises red laser diode 9, green laser diode 10, and blue laser diode 7. A full spectrum mirror 4, a red passing and green reflecting dichroic filter 5, and blue reflecting, red and green passing dichroic mirror 6, respectively, are positioned adjacent the diodes. Element 7 is a laser housing and heat sink for the module, and element 8 is a laser flexible circuit board to which the laser diodes are mounted.

Although not shown, the scanner may include despeckler module comprising a micro lens array (MLA), a despeckler drive motor, a despeckler housing, a diffuser disk 15 (that acts as a despeckling element), and an achromatic lens (a "doublet" or "collimating" lens). The diffuser disk spins in front of the laser.

Figure 3:
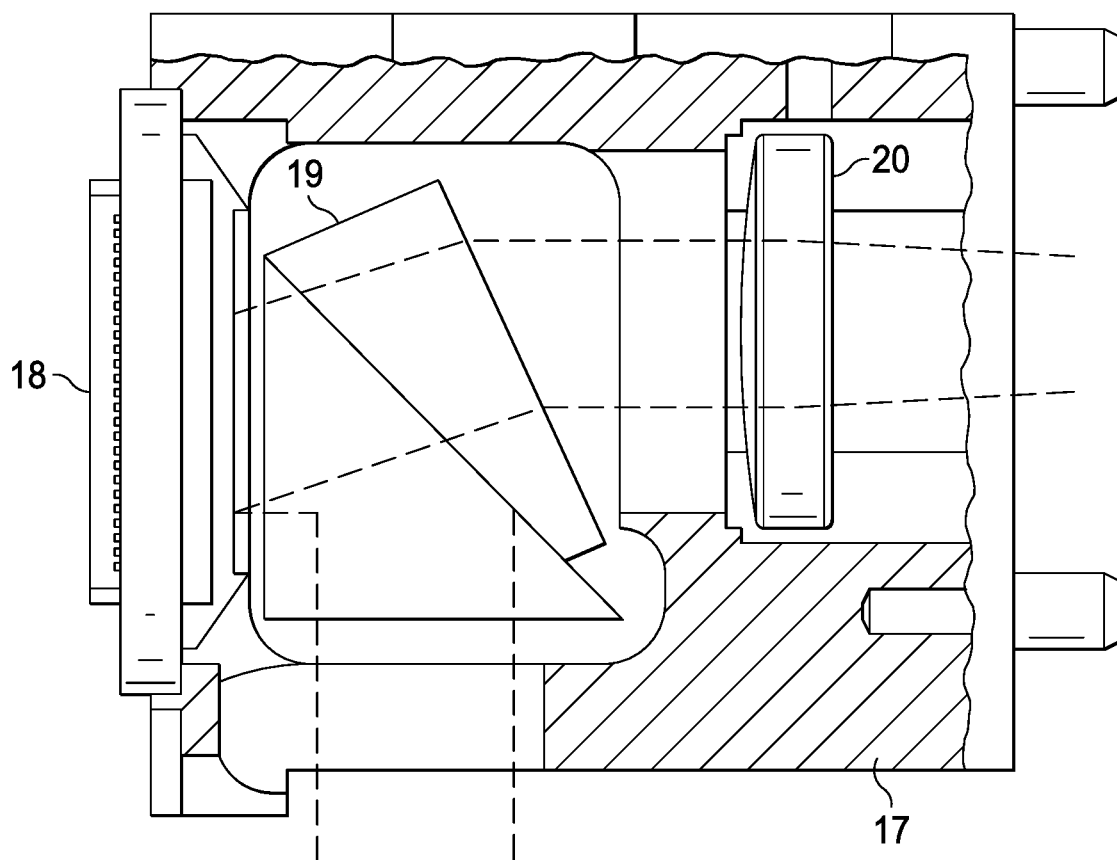
FIG. 3 depicts a light projection module of the scanner.

FIG. 3 depicts a projection module showing the light paths. As shown, the projection module comprises a TIR housing 17, a laser light spatial modulator chip 18, a Total Internal Reflection (TIR) prism 19, and a tele-centric lens 20. As depicted, preferably the light comes into the module normal to the modulator chip surface; that light is then moved off-axis by the TIR prism 19. This configuration enables the size of the overall optics system to be substantially reduced, thereby enabling the overall scanner to be reduced in size.

Figure 4:
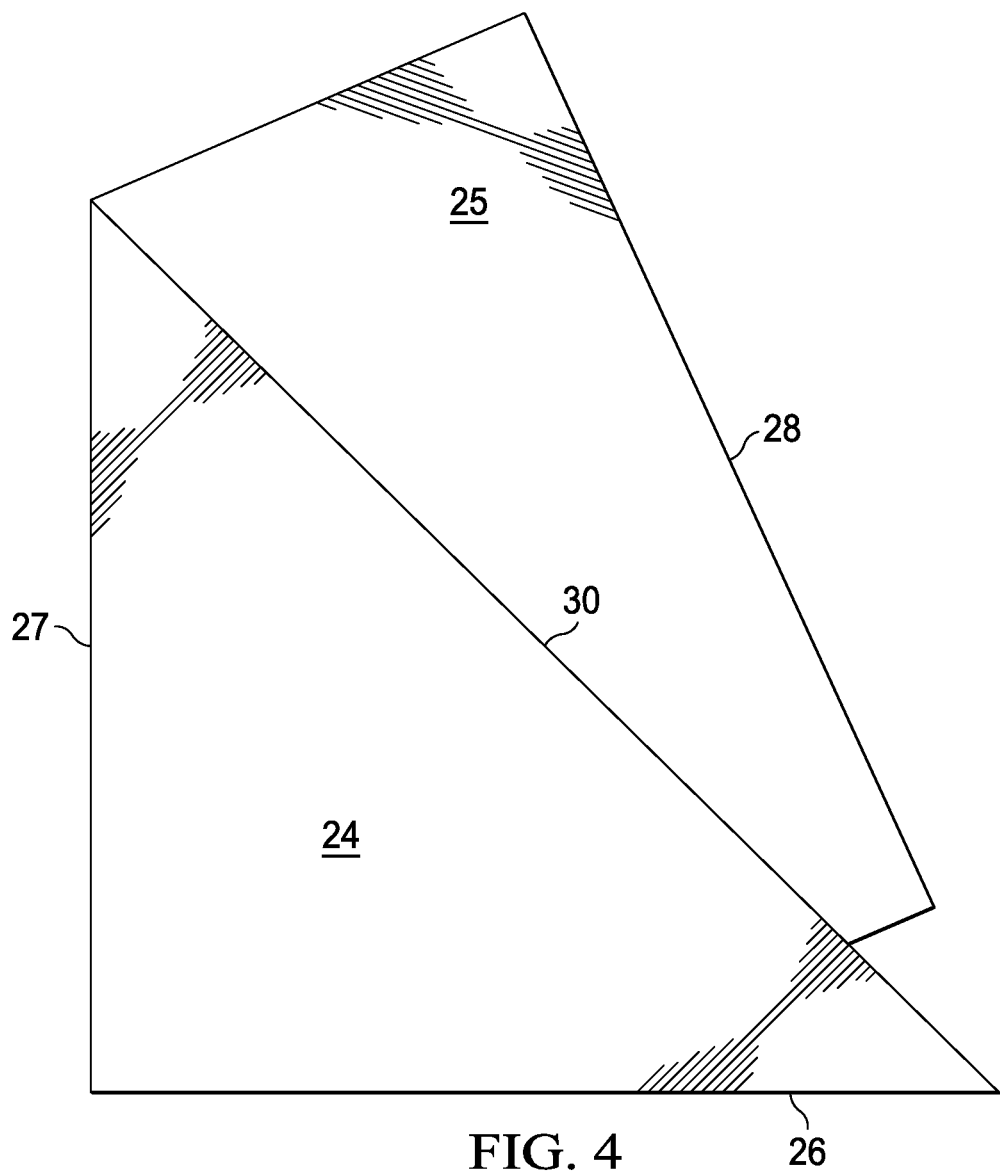
FIG. 4 depicts a preferred construction of the TIR prism in the light engine module of the scanner.
Figure 5A:
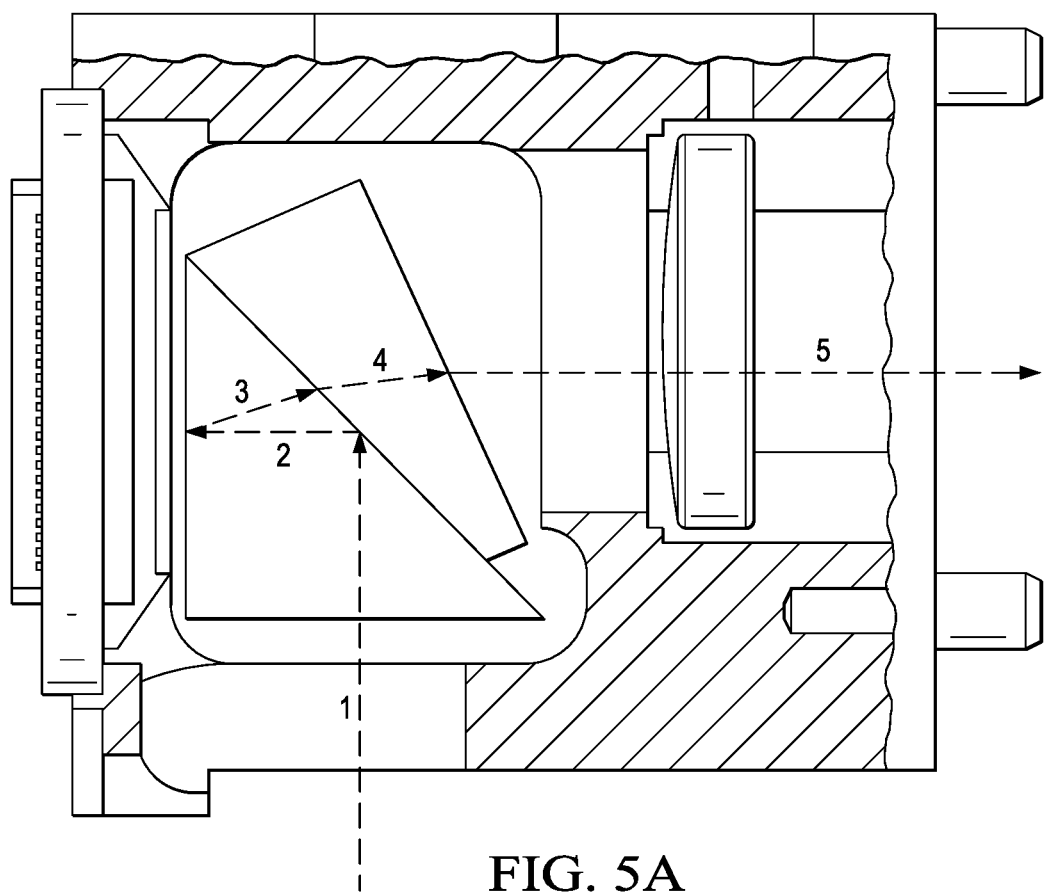
FIG. 5A depicts the beam path through the light engine module for light that is directed at greater than normal and thus projected to the rest of the optical system.
Figure 5B:
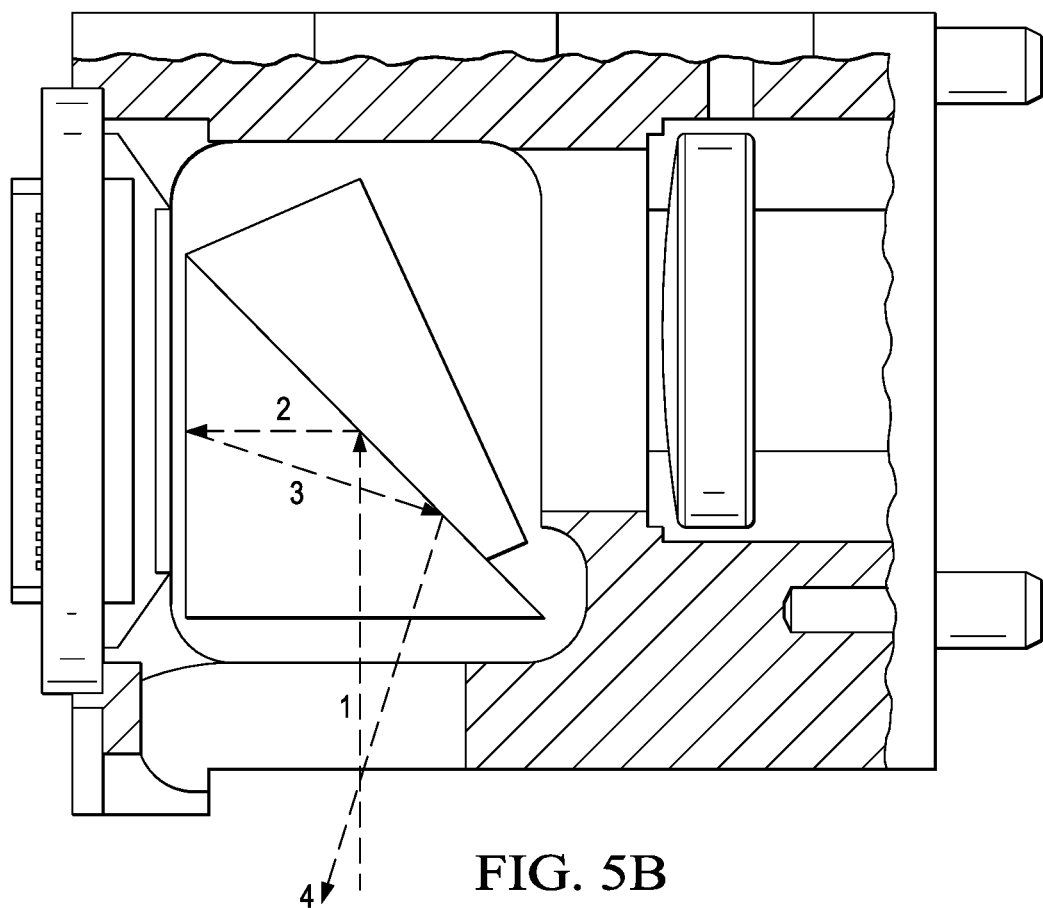
FIG. 5B depicts the beam path through the light engine module for light that is directed at less than normal and thus not projected.

The following provides additional details regarding the Total Internal Reflection (TIR) prism shown in FIG. 3, as well as its principle of operation. As depicted in FIG. 4, the TIR prism preferably is comprised of two pieces of glass 24 and 25, which pieces preferably are glued together with a very small air gap between them. The TIR prism is configured to transmit light that comes into the prism at a certain range of angles, and to reflect light that comes in at a different angle. In particular, and with reference to FIG. 4, and FIGS. 5A and 5B, light enters the prism at a normal to a first transmitting surface 26 and is largely reflected off of the TIR surface 30. This light is transmitted out of a second transmitting surface 27 onto a DMD surface 28, which will direct the light either at an angle greater than normal or less than normal depending in the DMD micro-mirrors' position. The light then again transits through the second transmitting surface 27. Light that exits the DMD surface 28 at an angle greater than normal is transmitted through the TIR surface 30 and is then transmitted out of the prism through a third transmitting surface 29. This is depicted in FIG. 5A. The third transmitting surface 29 is angled such that the exiting light is transmitted normal to the remaining projection path. Light that is reflected at an angle less than normal reflects off of the TIR surface 30 and is not projected through the system. This is depicted in FIG. 5B.

Thus, the TIR prism preferably is comprised of two prisms that are configured as shown, preferably with a few micron air gap there-between. The first prism 24 is a triangle (or right angle) prism comprising one angle at 90° and two other equal angles (at 45°), and it is formed of a material selected to ensure total internal reflection at surface 30. The second prism 25 is also a triangle prism, and it is formed in a shape of a wedge prism in which the wedge angle and material are designed to make the exiting laser beam parallel to the optical axis. Other than the 90° angle, the second prism has angles of approximately 21 and 69 degrees. As noted, preferably the prisms are bonded together with a small air gap along the surface 30. Preferably, the prisms are sized to ensure that there is a sufficient optically-clear aperture to cover the pattern size of laser beam. As noted above, the laser beam enters the first prism 24 at normal incident angle, and it is internally reflected (totally) by the 45 degree TIR surface 30 such that the beam then hits on the light modulator. When the modulator is turned on, and when each individual mirror turns +8 degree, then the laser beam is reflected back to prism 24 through to the 45° TIR surface 30. Due to the DMD angle, there is no internal reflection at the surface 30 of prism 24.

Thus, the laser beam travels through the first prism and reaches the second prism 25, where it is then bent by the third transmitting (back) surface such that the laser beam is parallel to the optical axis and goes through to the rest of the optical path. As noted above, this operation is depicted in FIG. 5A. When the DMD is at a parked position of 0° degree or at OFF position of angle of −8° degree, the laser beam does not make it through the 45° surface 30 of the first prism due to total internal reflection.

The above-described manner of arranging the TIR configuration enables both the DMD chip and the CCD (or CMOS-based) chip to be positioned in a vertical plane, and it simplifies the mechanical and electrical packaging and assembly. In part due to this construction, the overall scanner is much more compact than prior devices of this type.

In an alternative embodiment, the relative positions of the two prisms are switched, in which case the exit laser beam is normal to the TIR surface of the 45° prism, and the DMD chip is in a horizontal plane and perpendicular to CCD (or CMOS) surface.

FIGS. 6A and 6B depict the scanner's optical system in additional detail. FIG. 6A is a plan view, and FIG. 6B is an elevation view. As best depicted in FIG. 6A, the scanner's optical system 40 is configured to include two (2) optical paths, namely, a laser projection path 41, and an optical imaging path 42. Generally, the laser projection path preferably comprises three (3) color (RGB) lasers 43, and a spatial light modulator 44 to project a structured laser light pattern and live view color illumination on the tooth surface. The optical imaging path 42 comprises a high speed and high resolution CCD (or CMOS) sensor 45 to capture the image of the laser light pattern projected on the tooth surface from a perspective view. The separation of the two optical paths (which are configured side-by-side as depicted) forms a triangulation between a projected laser light pattern and the CCD optical imaging such a 3D shape of the tooth surface can be determined based on well-known triangulation principles. Preferably, both the projecting lenses 46 and the imaging lenses 47 each include the same four lens group and are optimized for high resolution, color correction, and tele-centric rays in the imaging space. In addition to the three (3) color laser diodes 43, the laser projection path includes laser collimating lenses 48, color combining filters 49, a micro-lens array homogenizer 50, a laser speckle reducer 51, an achromatic doublet lens 52, and the reflective TIR (Total Internal Reflection) prism 53 (as previously described). At the end of the scanner tip, the transmitted light is reflected off mirror 54.

Preferably, the depth of the field (approximately 15 mm) in the optical imaging path is designed based on controlling of aperture stop size and focal length. The depth of the field (e.g., approximately 15 mm) in the laser projection path is designed based on a slit aperture stop (as will be described in more detail below) to achieve sharp laser lines and bright laser output. The field of view (e.g., approximately 17 mm×9 mm) is designed based on the selected CCD sensor and spatial light modulator size, tip mirror size, optical magnification and total optical length. Preferably, a small imaging aperture stop and projection aperture stop located at the front of the optical system and without using any glass window, and preferably all of the lenses are attached to the main mechanical housing to avoid fogging in the optical path with the tip mirror, which is preferably heated.

Without intended to be limiting, representative optical design parameters of the scanner are as follows: effective focal length (26.6 mm), triangulation angle (6.55°), magnification (1/3.6×), field of view (17.6 mm×9.2 mm), CCD sensor size (4.736×3.552 mm with 7.4µ m pixel, 200 fps), spatial light modulator (0.3" with 10.6 µm pitch in column), color (3 lasers with RGB color), contrast (on and off mirror switching), uniformity (flat-top illumination with micro lens array).

Preferably, and with reference again to FIG. 1, the scanner tip 2 and data cable 3 are detachable and are replaceable components. The data cable 3 that attaches the scanner to a computer is a USB 3.0 data cable preferably attached to the remainder of the device by a bayonet lock style connector.

In operation, scanning software resident on an associated computer (e.g., desktop, laptop, or the like) extracts a 3D point cloud from the captured data, aligns the 3D point cloud to previously captured data, and renders to a display screen (or other output). This process is repeated as the user continues to scan. The system then allows the user to bring the restored anatomical data into a design tool. Through the use of the software, the user then designs a restoration (e.g., a crown) to fit the anatomical features.

Preferably, the scanner tip's mechanical design is a one-piece plastic housing, preferably with no external seams. It may also include an orientation marking to facilitate use. A mirror in the tip preferably is heated to prevent fogging, which would otherwise negatively impact the clinical experience. By rotating the body relative to the tip, the tip can be removed for service or replacement. Electrical connectivity to the heated mirror is provided by a connector structure.

Preferably, the RGB lasers in the scanner are color-balanced to produce a desirable image as is now described. In particular, the approach herein uses color calibration via laser emitter balancing. The following describes an approach to this calibration process.

Typically, the frames used to capture the data for the 3D model are partially-illuminated frames. To facilitate the operation of the device and provide live video as feedback to the operator (as well as the 3D-computed data), typically the scanner uses a sequence of patterns throughout which full illumination frames are selectively interspersed. A full illumination frame involves all or substantially all lines being turned on, as compared to a partially-illuminated approach, wherein only some lines are projected. In a full illumination frame, in effect there is no pattern. The partially-illustrated frames provide the data from which the 3D coordinates of the surface are determined. A technique for rendering frames in this manner is described in U.S. Pat. No. 7,184,150, the disclosure of which is incorporated herein by reference. In contrast, the full illumination frames are used for texturing the 3D model generated by the partially-illuminated frame data. In one sequence, a first set (e.g., six) pattern frames are used, interspersed with a second set (e.g., three) illumination frames, for a sequence total of nine total CCD frames. A software traffic shaper is then used to separate captured frames in two streams, namely, a live preview stream, and a data processing stream from which the 3D model is generated. If necessary, e.g., for computational or storage efficiencies, the live preview stream can give up priority and drop some frames when the CPU work load exceeds a certain limit.

As noted above, the intraoral scanner described herein may be provided as a standalone scanner, or as part of a CAD/CAM system. In one non-limiting implementation, the scanner is part of a CAD/CAM system that uses dental CAD software, such as E4D Design Center, executing on a laptop or desktop machine, optionally together with specialized milling machine hardware driven by machine control CAM software. The dentist first prepares a patient's damaged tooth anatomy (using standardized dental practices) to receive a dental restoration including, but not limited to, an inlay, an onlay, a veneer, a crown or a bridge. Once the preparation has been made, the dentist uses the scanner described and illustrated herein to capture a digital impression of a patient's dental anatomy. Once the digital impression has been captured the dentist is presented with an "initial proposal" restoration by the automated software. This initial proposal preferably automatically selects an appropriate tooth anatomy, and it sizes it to fit onto the preparation and within the patient's existing "good" anatomy. This initial proposal is then customized by the dental professional, typically using specialized software tools to adjust and modify the design, with the goal of ultimately achieving an optimized design that fits into the patient's anatomy. Once the final 3D model of the tooth has been achieved, it is sent electronically to a milling machine (or third party), which then generates the actual restoration from the design.

The RGB lasers in the scanner may be selectively controlled (or turned off) to produce any particular color (e.g., blue, purple, etc.). In another embodiment, the particular color utilized for scanning is a function of the material to be scanned.

The scanner tip also may be customized as needed (e.g., to include additional devices or elements) depending on the scanning application.

Integrated Optical Coherence Tomography (OCT)

As described above, and according to this disclosure, the above-described scanner is augmented to also carry optical components to facilitate OCT-based scanning, optionally at the same time the RGB-based scanning is carried out. The latter operation is particularly desirable as it enables the scanning to be performed in a one-pass manner, e.g., with surface data being collected by the RGB scan and data representing the volume underlying the surface being captured by the OCT scan. The one-pass operation is facilitated by registering the datasets (typically, each 3D) obtained from the separate scans and thereby greatly reducing the OCT scan volume required.

Figure 7:
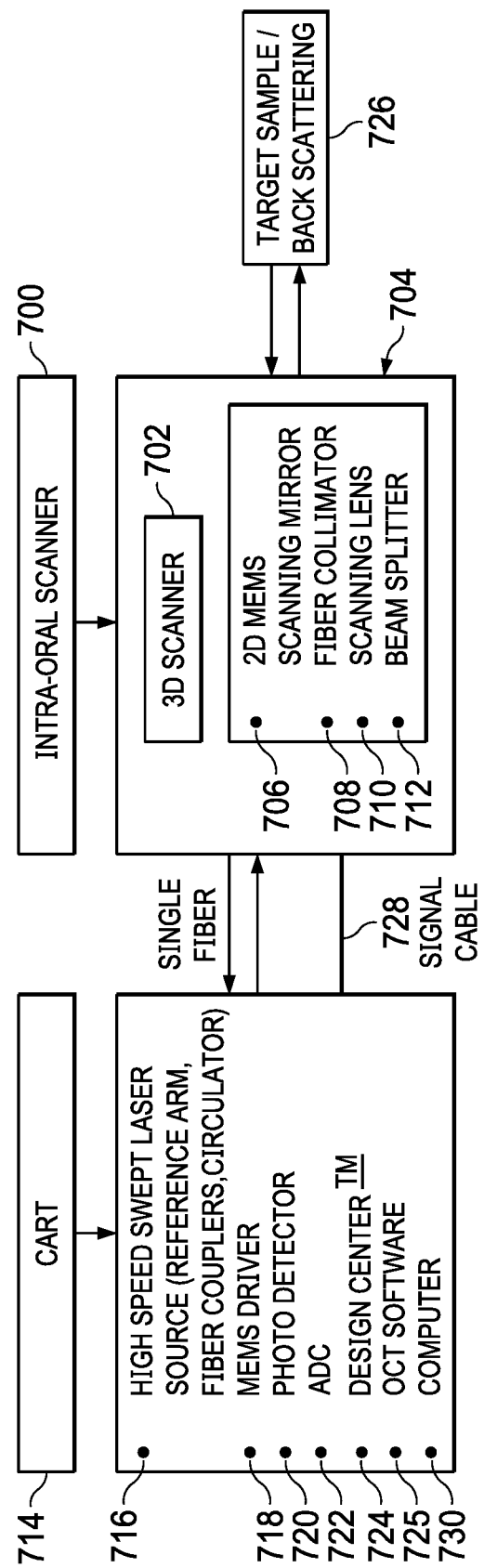
FIG. 7 is a block diagram of an overall system in which the techniques of this disclosure may be implemented.

FIG. 7 is a block diagram of a system that includes the integrated RGB- and OCT-based scanners. As depicted, the intra-oral scanner 700 comprises the 3D RGB-based scanner 702, together with the OCT-based scanner 704. As will be seen, the OCT scanner 704 comprises a set of optical elements, namely, a 2D MEMS scanning mirror 706, a fiber collimator 708, a scanning lens 710, and a beam splitter 78. The intra-oral scanner 700 is coupled to the rest of the system typically supported on a physical cart 714. To support the OCT scan, the cart 714 includes a high speed swept laser source 716 (namely, a reference arm, fiber couplers, and circulator), which are coupled to the OCT components in the scanner preferably via a single mode fiber 717. The cart also supports a MEMS driver 718, a photodetector 720, an analog-to-digital converter 722, and the software 724 and 725 used to process the data received from the respective REG-based and OCT-based scanning. These programs 724 execute in hardware, e.g., in a computing system (a laptop, a desktop, a tablet or mobile device, etc.) 730 as has been described. A representative commercial system that includes such processing components is E4D Design Center, although use of this commercial solution is not a requirement. Any CAD/CAM system that provides a user interface on which images are rendered is suitable. In operation, the intra-oral scanner 700 captures data from target sample 726 via back scattering, the data is returned to the processing systems via signal cable 728 and processed and used to render images on a suitable graphical user interface (GUI) and/or to control other CAD/CAM subsystems (e.g., a dental mill).

Figure 8:
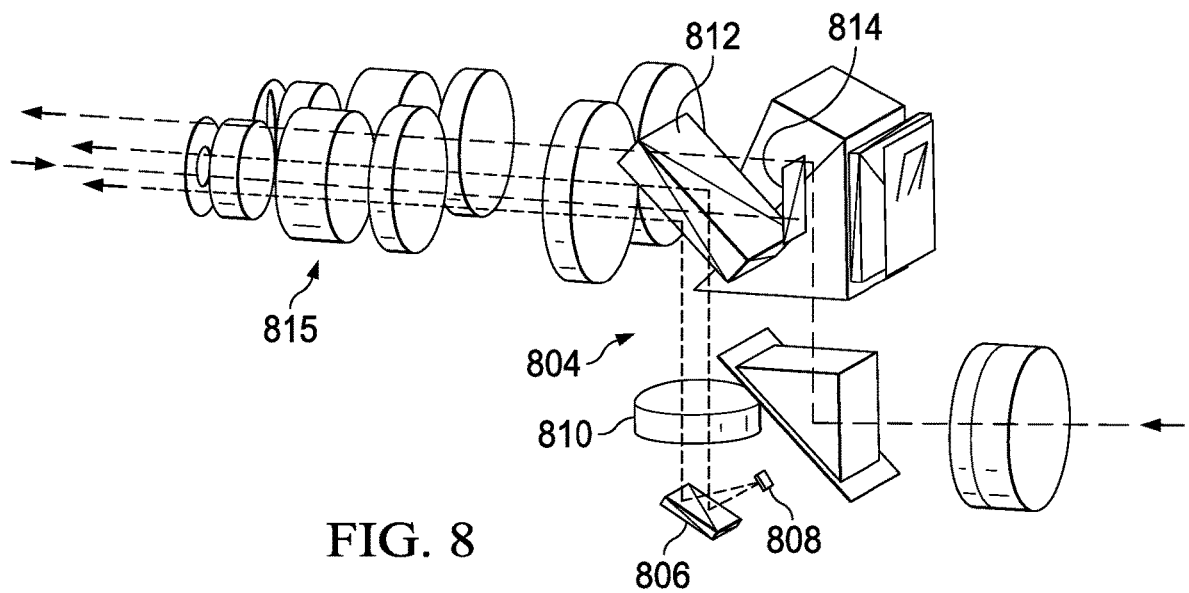
FIG. 8 depicts a first embodiment of the optical system component of an intra-oral scanner than integrates OCT and RGB-based scanning according to this disclosure.

FIG. 8 depicts the optical components of the OCT scanner integrated within the scanner previously described above. As depicted, the OCT scanner 804 comprises fiber collimator 808, two-dimensional (2D) MEMS scanning mirror 806, fiber collimator 808, an aspherical scanning lens 810, and a beam splitter 88. The imaging camera 814 that is used for the RGB scanner is also visible in this view. In one embodiment, and to facilitate the OCT scanning, a high speed swept laser beam at a center wavelength (e.g., 910+/−50 nm) is delivered through the single mode fiber (717 in FIG. 7) to the OCT scanner. The laser beam is collimated by the fiber collimator 808 and aligned to the two-dimensional (2D) MEMS scanning mirror 806, which scans the laser beam in X and Y directions. The scanned laser beam is coupled in a telecentric beam using the aspherical scanning lens 810. The telecentric laser beam is then reflected from the beam splitter 88 at a given angle (e.g., 45°), which reflects wavelengths at the center wavelength but transmits RGB wavelengths used in the 3D optical scan. The reflected beam for the beam splitter is projected through the lens projecting system previously described. That lens projecting system preferably includes lenses 815 with dual band reflective anti-reflection coating for both the center wavelength and RGB wavelengths to pass through. The tip mirror in the device also reflects the center and RGB wavelengths. In operation, a backscattering beam from a test sample travels through a same path to the fiber and is combined with a reference at a photodetector to generate an OCT image. Independently, and without interfering with the OCT laser and signal, the scanner projects RGB laser patterns and, using camera 814, captures 3D images using a CCD sensor or the like. As previously described, the OCT and RGB-based scanner are configured to operate both independently, but preferably they are configured and controlled to work in a combined manner to provide a one-pass operation to facilitate enhanced 3D imaging and dental diagnosis. In particular, when the two scanners are used together, the 3D data obtained from the OCT scan is registered with the 3D data obtained from the RGB-based scan by virtue of the returned beams being carried over the same optical return path. Preferably, the 3D surface data is used to align the volume data, such that the OCT scan operates over a much sparser scanning volume than would otherwise be required if the OCT scan were carried out separately. By combining and using the scanners in this manner, there is less stitching of data required to build the output images, thereby enabling a "one-pass" operation.

As depicted in FIG. 8, the outbound and return optical paths for the OCT scan are the same. The outbound optical path for the RGB scan is parallel to the outbound optical path for the OCT scan, but preferably the return optical path for the RGB scan is the same return optical path that the OCT scan uses. The scans do not interfere with one another, however, due to the different wavelength ranges utilized for each of the sources (910+/−50 nanometers for the OCT, and 400-700 nm for the RGB). These ranges are provided by way of example only and are not intended to be limiting.

Figure 9:
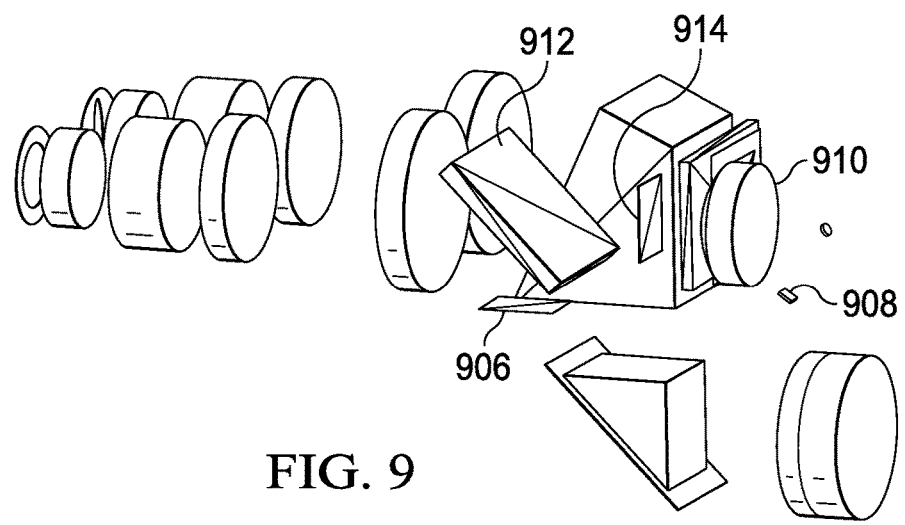
FIG. 9 depicts a second embodiment of the optical system components of an intra-oral scanner that integrates OCT and RGB-based scanning according to this disclosure.

FIG. 9 depicts an alternative embodiment in which the two-dimensional (2D) MEMS scanning mirror 906, fiber collimator 908, aspherical scanning lens 910, and a beam splitter 98 are positioned as shown. Thus, in this embodiment, the scanning mirror 906 and the aspherical scanning lens 910 are positioned in-line, relative to the imaging camera 914 used for the RGB scanner.

The OCT scan uses infrared light, while the RGB scan uses visible light, and the dual band optics (such as depicted in FIG. 8) enable the scans to occur concurrently without interfering with one another. The OCT scan travels through the dual band lenses, with the scan being returned through that same path; the RGB scan travels through the dual band lenses on the output path (directed to the target), with the scan being returned through the parallel detection path. By shooting both scans through the same optical (outbound) optical path, the approach herein enables simpler registration of the resulting scan data (by the detection software). In particular, the RGB and OCT cameras are calibrated with respect to one another (in part because they use at least some of the same optical components) so that, in effect, the captured data itself comes in pre-aligned. With respect to a given target, the RGB scan captures 3D surface data, while the OCT scan captures 3D depth data (with respect to the surface depicted by the surface data). This dual scanning approach thus provides significant efficiencies and improved results for the operator.

Thus, according to the technique of this disclosure, in a single scan session a dentist obtains both 3D surface data and 3D volume data (e.g., below a tooth/gingival surface), thereby enable a full evaluation and saving time and equipment/consumable costs. By using a single scan, the patient is exposed to less radiation. Without limitation, the following indications are then facilitated. In particular, the OCT scanner provides for enhanced margin detection of the 3D geometry captured by the structured light scan, thereby digitizing through blood, saliva and thin gingiva tissue. This enables the dentist or other professional to save time, materials and equipment. Using the OCT scanner, the user does not have to retract tissue to obtain a scan of the underlying volume. With this approach, the margin is clearly visible. The OCT scanner can be used to detect, track and analyze a cementation gap/fitting of a dental restoration, to provide margin gap detection, to detect early caries, to detect early demineralization, to detect and size cavities, to detect gingival pockets, to detect cracks, to facilitate plaque diagnosis, and to facilitate oral cancer screening and detection. In a preferred embodiment, 3D pictures of a surface region and that are obtained using the structured light-based scanner are enhanced using the OCT scanner to enable the user to find a margin. Moreover, during processing of the scan data returned over the common path, the surface data is used as necessary to reduce the amount of raw data captured from the OCT scan and that would otherwise need to be evaluated. Thus, for example, using the surface data, certain portions of the underlying scan (e.g., air) can be safely ignored (filtered) . In this manner, surface and underlying volume data are intelligently stitched together in a computationally-efficient manner, thereby speeding up processing of the scan data returned. In effect, the surface data scan is used to augment the volume data scan (or vice versa), such that the OCT data that is not indicative of underlying structure need not be fully processed.

The preferred design specifications for the OCT scanner are as follows. The laser source has a sweep speed greater than 1.5 MHz, a center wavelength of 910 nm, a sweep wavelength range of 80 or 100 nm, an A-scan resolution equal to 20 micro-meters or better, a laser output power greater than 30 mW, and a coherence length greater than 30 mm. The MEMS scanning mirror is a dual axis device, with scanning mirror size equal to 0.8 mm, an optical scanning angle equal to +/−7.25° in X, +/−7.25° in Y, scanning speed in X (fast axis) equal to 2.5 kHz, and scanning speed in Y (slow axis)=25 Hz. In the first embodiment, the preferred laser beam size from the fiber collimator is 0.8-1.0 mm, with transverse resolution=38 micro-meters (Gaussian beam), and a field of view=7 mm×7 mm. In the second embodiment, the preferred laser beam size from the fiber collimator is 0.8-1.0 mm, with transverse resolution=60 micro-meters (Gaussian beam), and a field of view=15 mm×8 mm. These characteristics are not intended to be limiting.

Typically, both sets of data are collected concurrently. Each scan path, however, typically is calibrated separately. Thus, e.g., the OCT scanner typically is calibrated as a function of the index of refraction of the material being scanned (e.g., blood, water, dentin, etc.).

The following are several representative algorithms that may be used to align the OCT data the data obtained from the 3D scan. These algorithms assume that the OCT scanning volume dimensions are known, and that a mapping between an OCT space and the laser scanning volume space is affine.

As a pre-alignment step, a lens calibration is performed. A calibration target is then set at a predetermined distance, e.g., based on OCT scanning volume specifications. Point correspondences for at least three (3) points on the of the calibration station are then selected. These are OCT volume points v1, v2 and v3 Scanning volume points s1, s2 and s3 are selected. If necessary, the OCT volume can be found by running an edge analysis algorithm that performs intensity thresholding and non-maxima suppression. From this operation, a depth of the OCT data set for the mapping can be determined. Then, point v I is translated to s1, point v2 to s2, etc.; this is defined as tvs. Then, a plane from v1, v2, v3 is defined as pv; the normal of this plane is nv. The quaternion of this normal is qv. Then, a plane from s1, s2, s3 is defined as ps; the normal of this plane is ns. The quaternion of this normal is qs. The algorithm then determines a resultant quaternion that maps qv to qs, which is defined as qvs. The routine then applies tvs and qvs to a mapping matrix defined as mvs. This is the matrix used to map OCT space into scanning volume space.

If a non-affine transformation is assumed, a surface mapping is used to map the points.

To this end, a surface mapping transformation iterates through different calibration station positions and develops a mapping table or surface that maps each point in the OCT volume to each point in the scanning volume. The edge detection algorithm described above can be used for this purpose.

Another option is to use real-time mapping. To perform real-time alignment, the following algorithm may be used. For each frame, generate an OCT surface from the OCT volume (e.g., using the edge detection algorithm); for each x, y position in the OCT volume, define a depth of that position z as the minimum depth that has an edge (thereby creating a set of OCT x,y,z tuples); and run ICP on the OCT points with the current scanning volume points, and use the resultant matrix as the transformation between OCT space and surface scanning space.

Variants

The dual scanner approach herein may have several variants.

In one variant, the OCT scan is done in 2D (e.g., using a single axis mirror instead of a dual axis mirror) instead of 3D. A 2D OCT-based scan is useful for diagnosis where details of a margin (e.g., with respect to a tooth) are not required.

In another variant, the OCT scan is done in 3D (or 2D), but instead of using a scanner based on structured light (such as the structured light-based RGB scanner described above), the visible scan is carried out using another source, such as a photogrammetry-based scanner, a confocal-based scanner, or the like.

Thus, and generalizing the approach herein, a dual scanner comprises first and second scanners that are configured in a housing in which they share optical components such that scans directed from the first and second scanners shoot (in whole or in part) through these shared optical components. Dual band optics are used as part of the shared optical components to enable the scans to be carried out concurrently and without interference. The resulting data captured (typically surface data captured by one scan, and depth data captured by the other scan) is then pre-aligned.

Having described our invention, what we claim is as follows.

The invention claimed is:

1. An intra-oral scanner, comprising:
a first scanner configured to operate in a first wavelength range to obtain first scan data from a surface of a target using a first optical path, the first scan data comprising a first three-dimensional image of the surface of the target, and the first scanner comprising a TIR prism comprising a first right triangle prism and a second triangle prism shaped like a wedge having angles of 90°, approximately 21°, and approximately 69°;

a second scanner configured to operate in a second wavelength range to obtain second scan data at video speed from a volume underlying the surface of the target using a second optical path, the second scan data comprising a second three-dimensional image of the volume underlying the surface of the target; and a housing configured to support the first scanner and the second scanner;

wherein a first portion of the first optical path is common with a first portion of the second optical path; and wherein a second portion of the first optical path is parallel to a second portion of the second optical path.

2. The intra-oral scanner according to claim 1 wherein the first and second wavelength ranges are non-overlapping.

3. The intra-oral scanner according to claim 1 wherein the intra-oral scanner is configured to align the first scan data with the second scan data.

4. The intra-oral scanner according to claim 2 wherein the intra-oral scanner is configured to align the first scan data with the second scan data.

5. The intra-oral scanner according to claim 1 wherein the intra-oral scanner is configured to register the second three-dimensional image with the first three-dimensional image.

6. The intra-oral scanner according to claim 5 wherein the first portion of the first optical path comprises at least a portion of a return path for the first scanner and the first portion of the second optical path comprises at least a portion of a return path for the second scanner.

7. The intra-oral scanner according to claim 4 wherein the first portion of the first optical path comprises at least a portion of a return path for the first scanner and the first portion of the second optical path comprises at least a portion of a return path for the second scanner to achieve registration of the second three-dimensional image with the first three-dimensional image.

8. The intra-oral scanner according to claim 1 wherein the first portion of the first optical path comprises at least a portion of a return path for the first scanner and the first portion of the second optical path comprises at least a portion of a return path for the second scanner to align the first scan data with the second scan data.

9. The intra-oral scanner according to claim 6 wherein the second portion of the first optical path comprises at least a portion of an outbound path for the first scanner and wherein the second portion of the second optical path comprises at least a portion of an outbound path for the second scanner.

10. The intra-oral scanner according to claim 8 wherein the second portion of the first optical path comprises at least a portion of an outbound path for the first scanner and wherein the second portion of the second optical path comprises at least a portion of an outbound path for the second scanner.

11. The intra-oral scanner according to claim 1 wherein the first scanner is a structured light line-based RGB scanner and the second scanner is an OCT-based scanner.

12. The intra-oral scanner according to claim 11 further comprising a detachable scanner tip and wherein the first scanner comprises a heated mirror disposed near the detachable scanner tip.

13. The intra-oral scanner according to claim 11 wherein the second scanner comprises an infrared swept laser configured to operate at a sweep speed of 1.5 MHz or greater.

14. The intra-oral scanner of claim 11 wherein the first scanner comprises a TIR prism comprising a first right triangle prism and a second wedge-shaped triangle prism.

15. The intra-oral scanner of claim 14 wherein the first right triangle prism in bonded to the second wedge-shaped triangle prism with a small air gap along a first surface of the first right triangle prism.

16. The intra-oral scanner of claim 15 wherein the first right triangle prism is formed of a material that allows for total internal reflection at the first surface.

* * * * *